US011000675B2

(12) United States Patent
Griffith

(10) Patent No.: US 11,000,675 B2
(45) Date of Patent: May 11, 2021

(54) CATHETER SNUGGER SYSTEM AND METHOD

(71) Applicant: Donald Griffith, Houston, TX (US)

(72) Inventor: Donald Griffith, Houston, TX (US)

(*) Notice: Subject to any disclaimer, the term of this patent is extended or adjusted under 35 U.S.C. 154(b) by 0 days.

(21) Appl. No.: 15/493,395

(22) Filed: Apr. 21, 2017

(65) Prior Publication Data

US 2018/0304046 A1  Oct. 25, 2018

(51) Int. Cl.
*A61M 25/04* (2006.01)
*A61M 25/10* (2013.01)
*A61J 15/00* (2006.01)
*A61M 27/00* (2006.01)
*A61M 25/02* (2006.01)
*A61M 25/00* (2006.01)

(52) U.S. Cl.
CPC .......... *A61M 25/04* (2013.01); *A61J 15/0042* (2013.01); *A61J 15/0049* (2013.01); *A61J 15/0057* (2013.01); *A61J 15/0065* (2013.01); *A61M 25/10* (2013.01); *A61M 25/1036* (2013.01); *A61M 27/00* (2013.01); *A61J 15/0015* (2013.01); *A61J 15/0073* (2013.01); *A61M 25/007* (2013.01); *A61M 2025/028* (2013.01); *A61M 2207/00* (2013.01); *A61M 2210/1085* (2013.01)

(58) Field of Classification Search
CPC ................ A61J 15/0015; A61J 15/0049; A61J 15/0042; A61J 15/0057; A61J 15/0065; A61J 15/0073; A61M 2025/028; A61M 2207/00; A61M 25/04; A61M 25/10; A61M 25/1036; A61M 25/02; A61M 2209/088; A61M 16/0875; A61M 2210/1085; A61M 25/007; A61M 27/00
See application file for complete search history.

(56) References Cited

U.S. PATENT DOCUMENTS 4,915,694 A * 4/1990 Yamamoto ............ A61M 25/02
604/180
9,173,777 B2 * 11/2015 Zurovcik ............. A61M 1/0011
(Continued)

OTHER PUBLICATIONS

"Special: Bladder Catherisation", UROLOG, Aug. 12, 2003, p. 10 (Year: 2003).*
(Continued)

*Primary Examiner* — Brandy S Lee
(74) *Attorney, Agent, or Firm* — The Law Firm of H. Dale Langley, Jr., P.C.

(57) ABSTRACT

A device for snugging a balloon of a catheter against an inner wall of an intra-corporeal lumen or surface serviced by the catheter includes a hollow column having a top end and a bottom end, forming a throughway sized to accommodate a tube of the catheter, and a flange extending from the bottom end of the hollow column generally perpendicularly to length of the hollow column. A slit is formed in the hollow column and the flange through which the hollow column is connectable to the tube of the catheter. The catheter is tugged to contact the balloon to the inner wall of the lumen, and the device is fixed to the tube of the catheter atop the skin of a body serviced by the catheter to tension pressure of the balloon against the inner wall.

3 Claims, 10 Drawing Sheets

(56) References Cited

U.S. PATENT DOCUMENTS

| | | | | |
|---|---|---|---|---|
| 2002/0077611 A1* | 6/2002 | von Dyck | ............... | A61F 5/442 |
| | | | | 604/333 |
| 2012/0095432 A1* | 4/2012 | Nath | ................... | A61J 15/0026 |
| | | | | 604/500 |
| 2015/0314112 A1* | 11/2015 | Griffith | ................. | A61M 27/00 |
| | | | | 604/540 |
| 2016/0038650 A1* | 2/2016 | Griffith | ................... | A61L 29/16 |
| | | | | 604/265 |
| 2016/0302999 A1* | 10/2016 | El-Haddad | .......... | A61J 15/0042 |

OTHER PUBLICATIONS

"Special: Bladder Catherterisation" (UROLOG) Aug. 12, 2003, Urolog.nl. p. 10.

\* cited by examiner

US 11,000,675 B2

CATHETER SNUGGER SYSTEM AND METHOD

TECHNICAL FIELD

The present invention generally relates to balloon catheters, and more particularly relates to snugger systems and methods for retaining a balloon retentive catheter or conduit within an intra-corporeal organ, cavity or potential space of a human body in a more water-tight and odor free manner.

BACKGROUND

In many medical, surgical and related applications, ostomy, conduits or tubes are placed within real or potential body lumens or spaces, so as to drain or inject fluids or particulate matter. Conventional ostomy practices include surgical creation of a passageway through the external covering, body wall muscles and/or integument and into intracorporeal body organs, spaces and potential space. The ostomy may be employed, for example, for access to or within an organ, vessel or other intra-corporeal feature, such as, for example, the bladder, stomach, kidney, intestine or other organ or feature. Various catheters or other intubation may be lodged and/or secured within the ostomy to aid drainage and/or injection.

Conventional catheters and other intubation devices can include balloons for retaining and/or immobilizing and securing the catheter or intubation device within the lumen of an organ, vessel or other intracorporeal space or feature. The balloon is inflated once the catheter or other intubation is positioned within the desired space or lumen. These catheters and other intubations can be prone to leakage from lack of water tightness with the lumen or space. This can cause cross-contamination of intra-lumen fluids with other body components and external features. These problems can lead to infection and egress of fluids or particulate matter into other organs, spaces or tissues.

It would therefore be desirable, and a significant improvement in the art and technology, to provide snugger systems and methods for retaining the balloon of a catheter or other intubation in contact with lumen mucosa to effectively seal the catheter or intubation against the mucosa.

SUMMARY

An embodiment of the invention is a device for snugging a balloon of a catheter against an inner wall of a lumen serviced by the catheter. The device includes a hollow column having a top end and a bottom end, forming a throughway sized to accommodate a tube of the catheter, and a flange extending from the bottom end of the hollow column, the flange extends generally perpendicular to length of the hollow column.

Another embodiment of the invention is a device including a hollow cylindrical column having a top and a bottom, the hollow cylindrical column is pliable, a flange connected to the bottom, the flange is pliable, and a connector to reversibly secure the hollow cylindrical column to the outer surface of the catheter.

Yet another embodiment of the invention is a method including providing a snugger device to an external portion of a tube of a catheter having a balloon inflated within a lumen of a body, tugging the catheter to bring the balloon into tensioned contact with an inner wall of the lumen or space and positioning the snugger device in contact with skin of the body in order to maintain tensioned contact of the balloon within the intracorporeal inner wall of the lumen or space.

Another embodiment of the invention is a method of manufacture including providing an external sleeve sufficient to accept the tube of a catheter, providing a flange connected to an end of the external sleeve, with or without forming a slit in the flange and the external sleeve for insertion of the external sleeve around the outer surface of the tube of the catheter.

Another embodiment of the invention is a snugger device having a fixation component that reversibly attaches and secures a snugger sleeve of the snugger device to the external surface of a drainage tube in various user-selected locations, the fixation component is selected from the group consisting of pins, latches, electromagnetic couplers, and Velcro connectors.

BRIEF DESCRIPTION OF THE DRAWINGS

The present invention is illustrated by way of example and not limitation in the accompanying figures, in which like references indicate similar elements, and in which.

DETAILED DESCRIPTION

Figure 1:
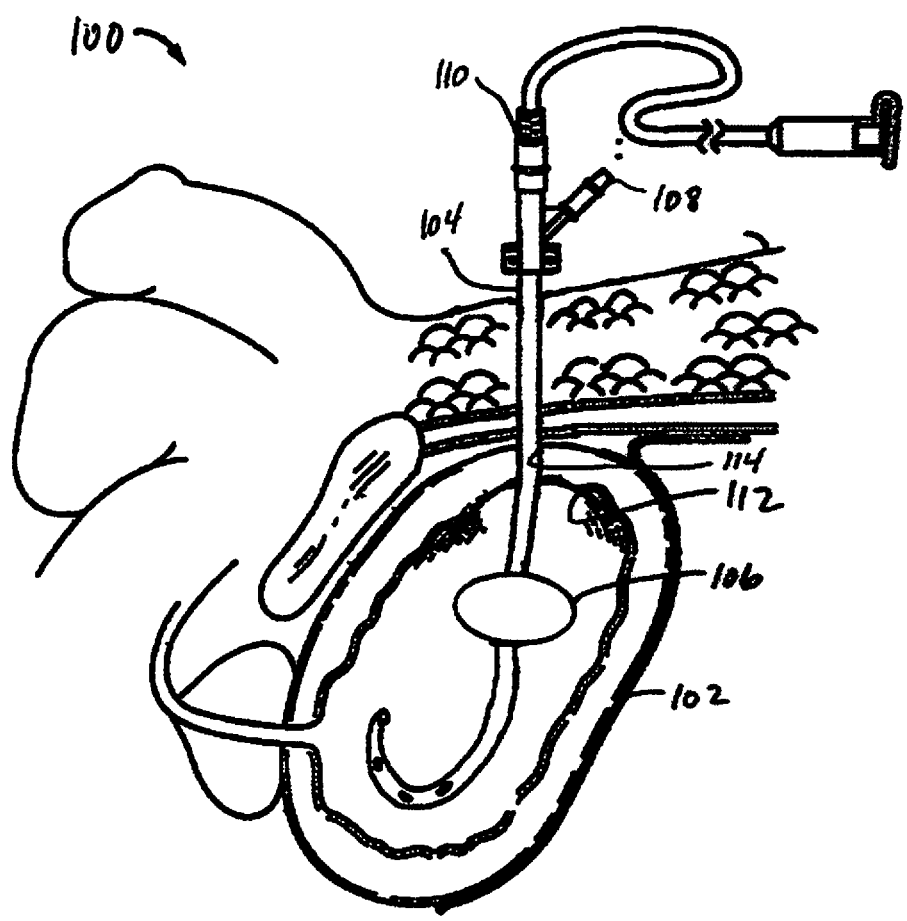
FIG. 1 illustrates a side view of a conventional urinary catheter with an inflated balloon of the catheter, positioned within the lumen of the bladder but not snugged in contact with the anterior mucosal surface of the bladder, according to certain embodiments of the invention.

Referring to FIG. 1, a conventional catheter 100 in use for drain of a bladder 102 includes a tube 104 and an inflated balloon 106 surrounding the tube 104 and positioned within the lumen of the bladder 102. The balloon 106 is inflated through an inflation port 108 of the catheter 100 and the tube 104 drains through a drain exit 110 of the catheter 100. The inflated balloon 106 is not snugly abutting the bladder wall 112 in the vicinity of an ostomy 114 for access to the bladder 102. The inflated balloon 106 may shift in position with respect to the bladder wall 112 as the patient moves. However, the inflated balloon 106 is not tensioned toward the bladder wall 112 to provide a more water tight connection between the bladder wall 112 and the inflated balloon 106.

Figure 2:
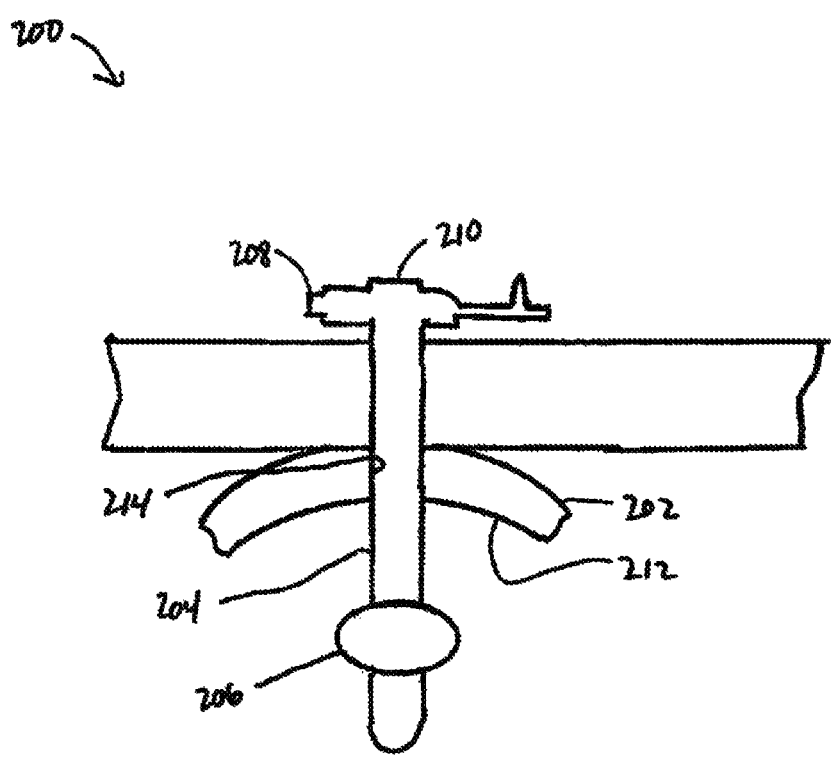
FIG. 2 illustrates a side view of a conventional gastrostomy catheter or feeding tube with an inflated balloon of the catheter, positioned within the lumen of the stomach but not snugged into contact with the anterior mucosal surface of the stomach, according to certain embodiments of the invention.

Referring to FIG. 2, a conventional gastrostomy tube 200 in use for feeding of a stomach 202 includes a tube 204 and an inflated balloon 206 positioned within the lumen of the stomach 202. The balloon 206 is inflated through an inflation port 208 of the gastrostomy tube 200 and the tube 204 is injectable through an injection port 210 of the gastrostomy tube 200. The inflated balloon 206 is not snugly abutting the stomach wall 212 in the vicinity of an ostomy 214 for access to the stomach 202. The inflated balloon 206 may shift in position with respect to the stomach wall 212 as the patient moves. The inflated balloon 206, however, is not tensioned toward the stomach wall 212 to provide a more water tight connection between the stomach wall 212 and the inflated balloon 206.

Figure 3:
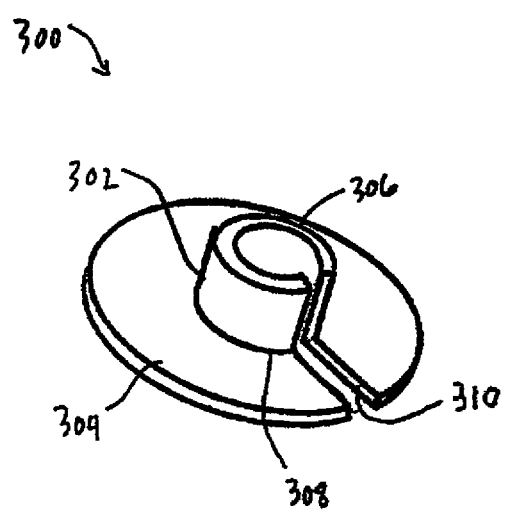
FIG. 3 illustrates a top and side perspective view of a snugger device, according to certain embodiments of the invention, with a slit in the cylinder and flange.

Referring to FIG. 3, a non-exclusive embodiment of a snugger device 300 includes a hollow column 302 connected to a flange 304. The column 302 has a top end 306 and a bottom end 308. The flange 304 protrudes from the bottom end 308 of the column 302 substantially generally perpendicular to the length of the column 302. The column 302 extends generally from a center of the flange 304. The column 302 and the flange 304 may include a side slit 310. The side slit 310 allows the column 302 to be wrapped around a tube of a catheter, feeding tube, or other intubation in use of the device 300. The column 302 is sized in cross-section to substantially surround the tube of the catheter, feeding tube, or other intubation when so wrapped. The flange 304 may be generally circular and may be sized with radius larger than that of the cross-section of the column 302. The flange 304 may rest on the skin or integument in use of the device 300.

Although the side slit 310 is illustrated, the side slit 310 is not needed if the column 302 of the device 300 is passed onto the tube prior to insertion of the tube into the body lumen. In such instance, the tube is pressed through the column 302 and the device 300 is located along the tube near an external portion of the tube. The tube is then fed into the body lumen, with the device 300 external to the body.

The device 300 may be formed of a silicone, rubber, plastic or other pliable material. The device 300 may be unitary or formed of separate connected pieces. The flange 304 of the device contacts the skin or integument when in use. The flange 304 applies a more consistent pressure of the device 300 against the skin or integument when the inflated balloon of a catheter or intubation is tensioned against an inner wall of a vessel serviced by the catheter or intubation. The column 302 is employed for securement of the device 300 to the catheter or intubation to maintain the inflated balloon of the catheter or intubation in tensioned contact with the inner wall of the vessel serviced by the catheter or intubation.

In operation, the device 300 is flexed to open the side slit 310 sufficient to allow the column 302 to be connected to the tube of a catheter, feeding tube, or other intubation that employs an inflated balloon or similar device to retain the intubation within a vessel lumen. Alternately, if the device 300 does not include the side slit 310, the device 300 is passed onto the intubation prior to insertion of the intubation into the body lumen. Once the column 302 is connected to the tube external to a body, the intubation is pulled to provide tension of the balloon or similar device against the vessel wall. The device 300 is secured in place along the intubation in contact with the skin or other integument of the body in order to maintain the tension of the balloon or similar device. The device 300 is secured, for example, by a safety pin passed through the device 300 and tube of the intubation, a latch, an electromagnetic coupler, Velcro of the inner surface of the device 300 and complementary Velcro on the outer surface of the tube, or another securement mechanism of the device 300.

Figure 4:
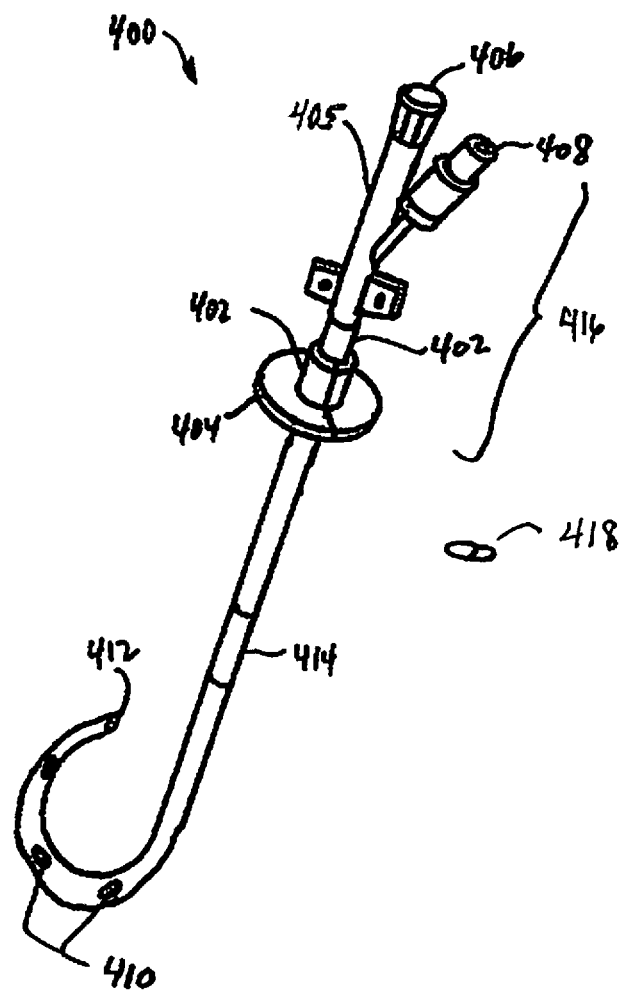
FIG. 4 illustrates a top and side perspective view of a snugger device connected to a catheter, according to certain embodiments of the invention.

Referring to FIG. 4, a snugger device 400 is placed on a tube 402 of a catheter 405. The snugger device 400 includes a column 402 connected to a flange 404. The catheter 405 includes a drain exit 406 and an inflation port 408. The drain exit 406 is in fluid communication with ports 410 located near a distal end 412 of the catheter 405. The inflation port 408 is in fluid communication with a balloon 414 surrounding the tube 402 of the catheter 405. The column 402 of the snugger device 400 substantially surrounds a circumference of the tube 402 of the catheter 405. The flange 404 of the snugger device 400 extends substantially perpendicular to the length of the tube 402.

In operation, the catheter 405 is inserted in conventional manner into an ostomy. The distal end 412 of the catheter 405 is lodged within a vessel, organ or other lumen. The balloon 414 is inflated through the injection port 408 to locate within the vessel, organ or other lumen. A fore portion 416 of the catheter 405 toward the drain exit 406 and the injection port 408 is located external to a body in which the catheter 405 is positioned. The snugger device 400 is placed on the tube 402 of the catheter 405 at the fore portion 416. The fore portion 416 is grasped and pulled to bring the inflated balloon 414 into tensioned contact with the inner wall of the vessel, organ or other lumen at the ostomy. The snugger device 400 is slid along the tube 402 of the catheter 405 to contact the skin or integument of a body in which the catheter 404 is lodged, in order to snug the inflated balloon 414 against the wall of the vessel, organ or other lumen. The snugger device 400 is attached to the tube 402 by a securement device, for example, a safety pin is passed through the column 402 of the device 400 and the tube 402 of the catheter 405, a latch is activated, an electromagnetic coupler is triggered, a Velcro of the inner surface of the device 300 is mated with complementary Velcro on the outer surface of the tube 402, or another securement mechanism 418 is employed to fix the snugger device 400 to the tube 402 to provide tension of the inflated balloon 414 against the inner wall of the vessel, organ or other lumen.

Figure 5:
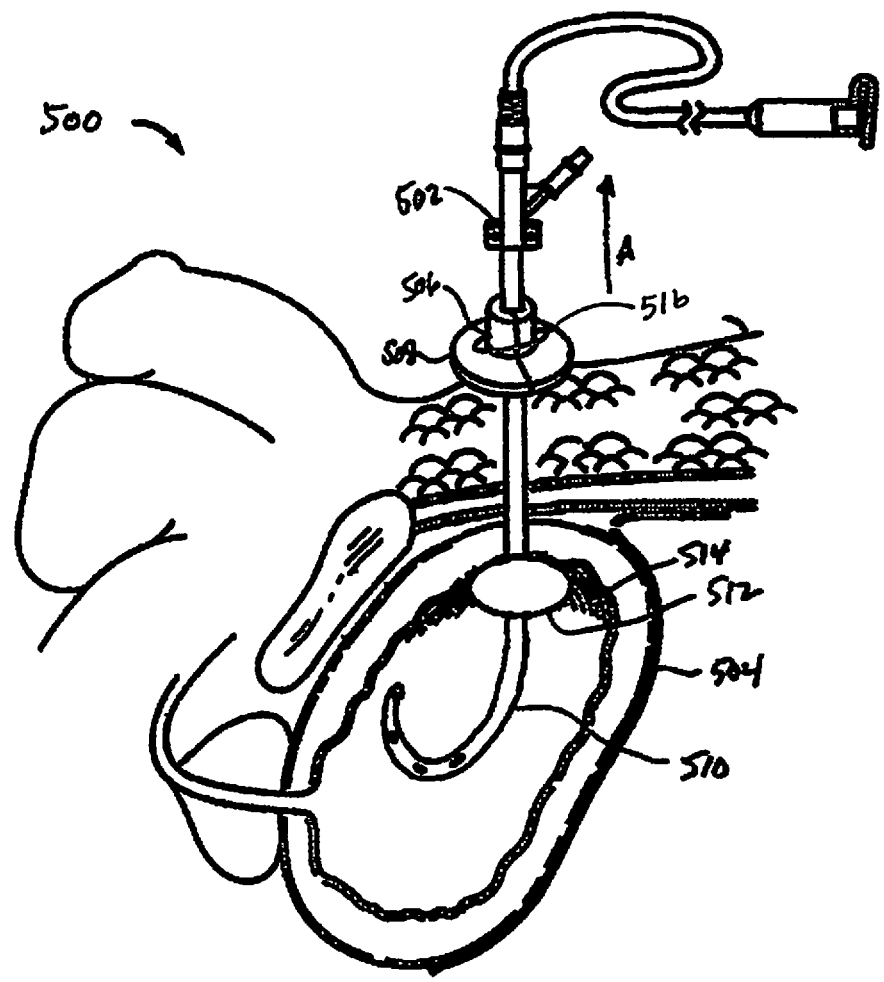
FIG. 5 illustrates a side view of a snugger device in use to tension and secure a balloon of a urinary catheter against the inner mucosa of the bladder, according to certain embodiments of the invention.

Referring to FIG. 5, a snugger device 500 is in use with a catheter 502 for urinary drainage of a bladder 504. The snugger device 500 includes a column 506 connected to a flange 508. A tube 510 of the catheter 502 is passed from an ostomy in the skin or other integument, through the body in the ostomy, and through the ostomy into the bladder 504. The catheter 502 has a balloon 512 surrounding the tube 506 toward an end of the catheter 502 inserted into the bladder 504. The balloon 512 is inflated to retain the end of the catheter 502 within the bladder 504.

The snugger device 500 is connected to the tube 510 of the catheter 504, external to the body in which the catheter 502 is placed. A slit 514 of the snugger device 500 allows the device to be deformed to accept the tube 510 in the column 506, or else if the snugger device 500 does not have the slit 514, the tube 510 is passed through the column 506 of the snugger device 500 prior to insertion of the tube 510 into the bladder 504. The flange 508 rests atop skin or integument of the body. An external portion of the catheter 504 is tugged (in the general direction of arrow A) to bring the balloon 512 into snug position with an inner wall 514 of the bladder 504 at the ostomy. The snugger device 500 resting on the skin or integument is secured 520 to the tube 510 of the catheter 504 in order to tension the balloon 512 against the inner wall 514 at the ostomy.

Figure 6:
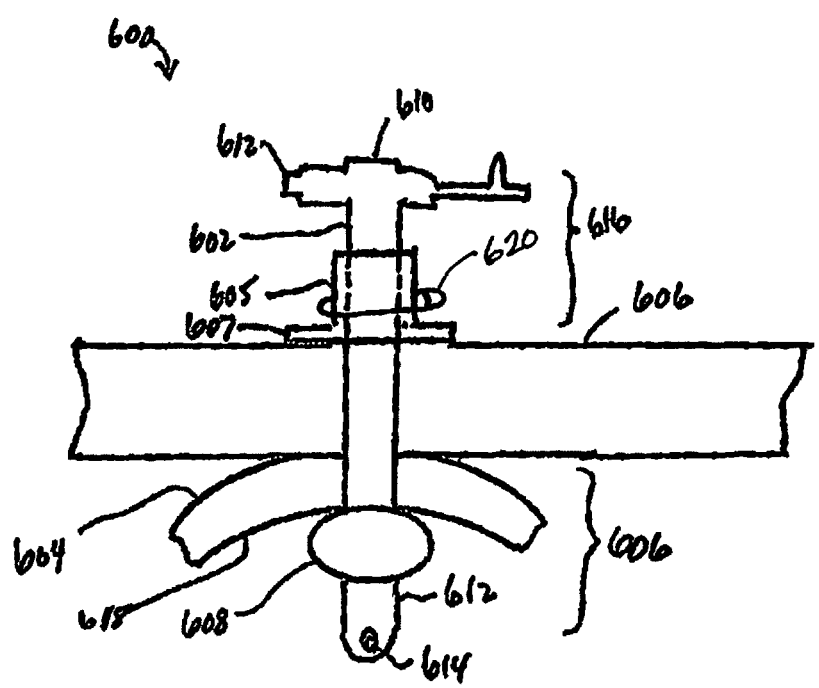
FIG. 6 illustrates a side view of a snugger device in use to tension and secure a balloon of a gastrostomy catheter or feeding tube against the inner wall of the stomach, according to certain embodiments of the invention.

Referring to FIG. 6, a snugger device 600 is in use with a gastrostomy feeding tube catheter 602 serving a stomach 604 inside an abdominal wall 606. The snugger device 600 includes a column 605 connected to a flange 607. The catheter 602 includes a balloon 608 surrounding a distal portion 610 of a tube 612 of the catheter 602. The catheter 602 includes a feeding inlet 610 and a balloon injection port 612. The feeding inlet 610 is in fluid communication with a port 614 at the distal portion 606. The injection port 612 is in fluid communication with the balloon 604 to allow inflation of the balloon 604 when the catheter 602 is positioned with the distal portion 606 in the stomach 604.

The snugger device 600 is connected to the tube 612 of the catheter 602 external to the body in which the catheter 602 is placed. A slit (not shown in detail) of the snugger device 600 allows the device 600 to be separated along the slit to accept the tube 612 in the column 605, or else if the snugger device 600 does not have the slit, the tube 612 is passed through the column 605 of the snugger device 600 prior to insertion of the tube 612 into the stomach 604. The flange 607 rests atop the skin of the abdominal wall 606. An external portion 616 of the catheter 602 is pulled to contact the balloon 604 to the inner wall 618 of the stomach 604 at the ostomy and provide tension of the balloon 604 against the inner wall 618. The snugger device 600 is slid along the tube 612 to contact the skin and retain tension of the balloon 604 against the inner wall 618. The snugger device 600 is secured to the tube 612, for example, by a safety pin passed through the column 605 and the tube 612, a mechanical latch, an electromagnetic coupler, a Velcro of the inner surface of the device 300 and complementary Velcro on the outer surface of the tube 612, or other securement device 620.

Figure 7:
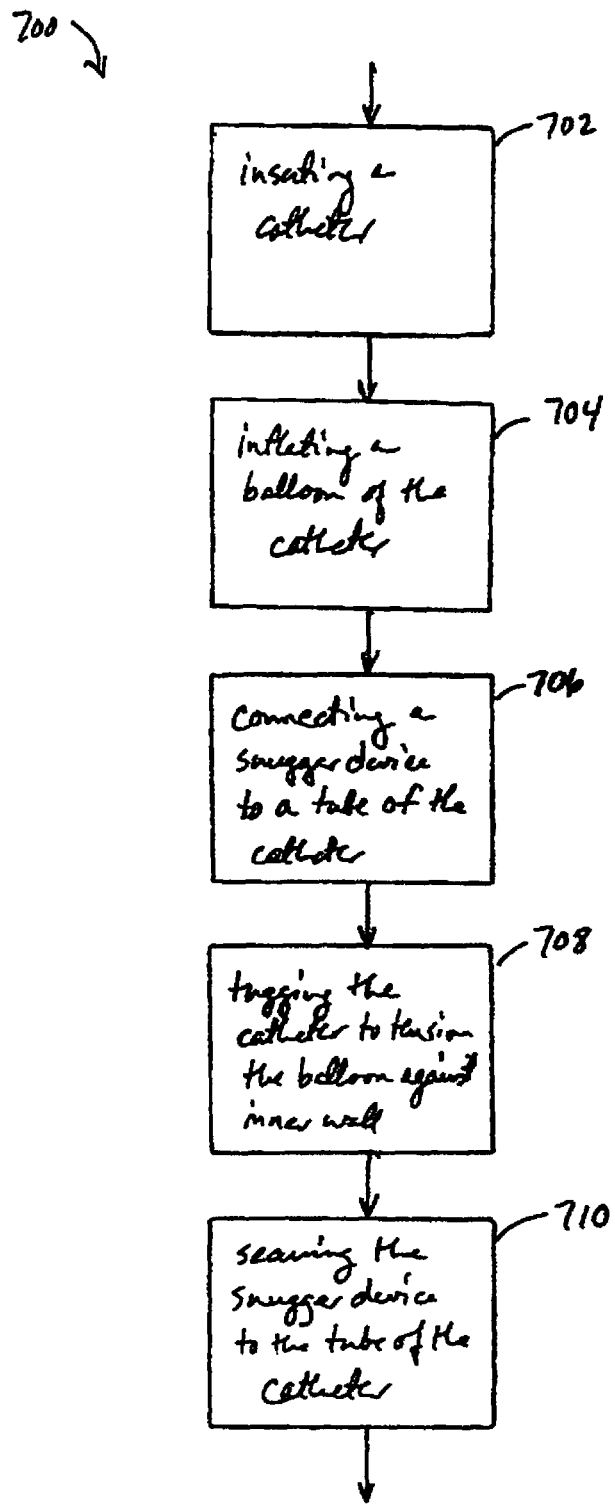
FIG. 7 illustrates a method of snugging a balloon of a catheter against the inner wall of a vessel, organ or other lumen, according to certain embodiments of the invention.

Referring to FIG. 7, a method 700 of snugging a balloon of a catheter against the inner wall of a vessel, organ or other lumen includes inserting 702 the catheter through an ostomy and extending into the lumen. Once the catheter is inserted 702, the balloon is inflated 704. A snugger device is connected 706 to an externally extending tube of the catheter. The externally extending tube of the catheter is tugged 708 to bring the inflated balloon into tensioned contact with the inner wall of the lumen. The snugger device is secured 710 to the externally extending tube atop the skin of the body, to maintain the tension of the inflated balloon against the inner wall of the lumen.

Although connecting 706 the snugger device to the catheter is illustrated as occurring after the catheter is inserted 702 and the balloon is inflated 704, the snugger device can alternately be connected prior to insertion of the catheter, by forming the catheter with the snugger device attached to the catheter, by passing a distal end of the catheter through the snugger device and sliding the snugger device into position along the catheter, or otherwise. As hereinafter described, an alternative snugger device may not include a slit and so would be connected to the catheter prior to insertion of the catheter into the lumen.

Figure 8:
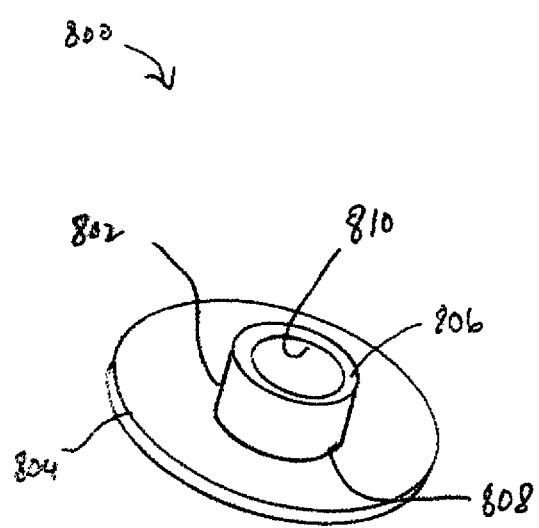
FIG. 8 illustrates an alternative snugger device, according to certain embodiments of the invention.

Referring to FIG. 8, an alternative snugger device 800 includes a hollow column 802 connected to a flange 804. The column 602 has a top end 806 and a bottom end 808. The flange 804 protrudes from the bottom end 808 of the column 802 substantially generally perpendicular to the length of the column 802. The column 802 extends generally from a center of the flange 804. The column 802 is sized in cross-section to accept an extent of a tube of a catheter, feeding tube, or other intubation, and slide along the intubation to a desired position. The flange 804 may be generally circular and may be sized with radius larger than that of the cross-section of the column 802. The flange 804 may rest on the skin or integument in use of the device 800.

The device 800 may be formed of a silicone, rubber, plastic or other pliable material. The device 800 may be unitary or formed of separate connected pieces. The flange 804 of the device contacts the skin or integument when in use. The flange 804 applies a more consistent pressure of the device 800 against the skin or integument when the inflated balloon of a catheter or intubation is tensioned against an inner wall of a vessel serviced by the catheter or intubation. The column 802 is employed for securement of the device 800 to the catheter or intubation to maintain the inflated balloon of the catheter or intubation in tensioned contact with the inner wall of the vessel serviced by the catheter or intubation.

In operation, the column 802 of the device 800 is passed onto an extent of a tube of a catheter or intubation, and the device 800 is slid into a desired position along the tube external to a body. Once the column 802 is connected to the tube, the intubation is fed into the lumen or potential space of a vessel for service of the intubation, a retentive balloon or similar device of the intubation is inflated within the lumen, and the intubation is tugged externally to the body to provide tension of the balloon or similar device against the inside of the vessel wall. The device 800 is secured in place along the intubation in contact with the skin or other integument of the body in order to maintain the tension of the balloon or similar device against the inner wall of the vessel. The device 800 is secured, for example, by a safety pin passed through the device 800 and tube of the intubation, a latch, an electromagnetic coupler, Velcro of the inner surface of the device 800 and complementary Velcro on the outer surface of the tube, or another securement mechanism of the device 800.

Figure 9:
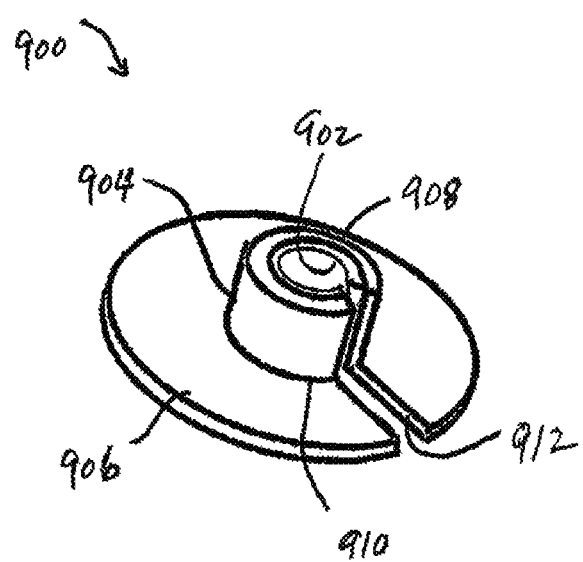
FIG. 9 illustrates a Velcro connector of a snugger device, according to certain embodiments of the invention.

Referring to FIG. 9, a non-exclusive embodiment of a snugger device 900 includes a connector 902 on an inner surface of a hollow column 904 of the device 900. The connector 902 is, for non-exclusive example, a Velcro segment connected to the inner surface of the column 904. The connector 902 may mate with a connector of a tube of a catheter or other intubation, such as, for non-exclusive example, a matching Velcro segment on an outer surface of the intubation. The device 900 includes the column 904 connected to a flange 906. The column 904 has a top end 908 and a bottom end 910. The flange 906 protrudes from the bottom end 910 of the column 904 substantially generally perpendicular to the length of the column 904. The column 904 extends generally from a center of the flange 906. The column 904 and the flange 906 may include a side slit 912. The side slit 912 allows the column 904 to be wrapped around a tube of a catheter, feeding tube, or other intubation in use of the device 900. The column 904 is sized in cross-section to substantially surround the tube of the catheter, feeding tube, or other intubation when so wrapped. The flange 906 may be generally circular and may be sized with radius larger than that of the cross-section of the column 904. The flange 906 may rest on the skin or integument in use of the device 900.

Although the side slit 912 is illustrated in the device 900, the side slit 912 is not needed in accordance with the snugger device 800 of FIG. 8. The snugger device 800 may be passed onto a tube of a catheter or other intubation prior to insertion of the tube into the body lumen. The snugger device 800 of FIG. 8 can be fitted with a connector (not shown in detail in FIG. 8), such as for non-exclusive example, a Velcro segment connected to an inner surface of the hollow column 904 of the device 800. In such instance, the tube is pressed through the column 904 and the device 900 is located along the tube near an external portion of the tube. The tube is then fed into the body lumen, with the device 900 external to the body, a retentive balloon or device of the tube is inflated or activated within the body lumen, and the connector is connected along the tube to provide tensioned engagement of the balloon or device to the inner wall of the lumen. The connector, if a Velcro segment, may connect, for example, to a corresponding Velcro segment attached to an outer surface of the tube.

Figure 10:
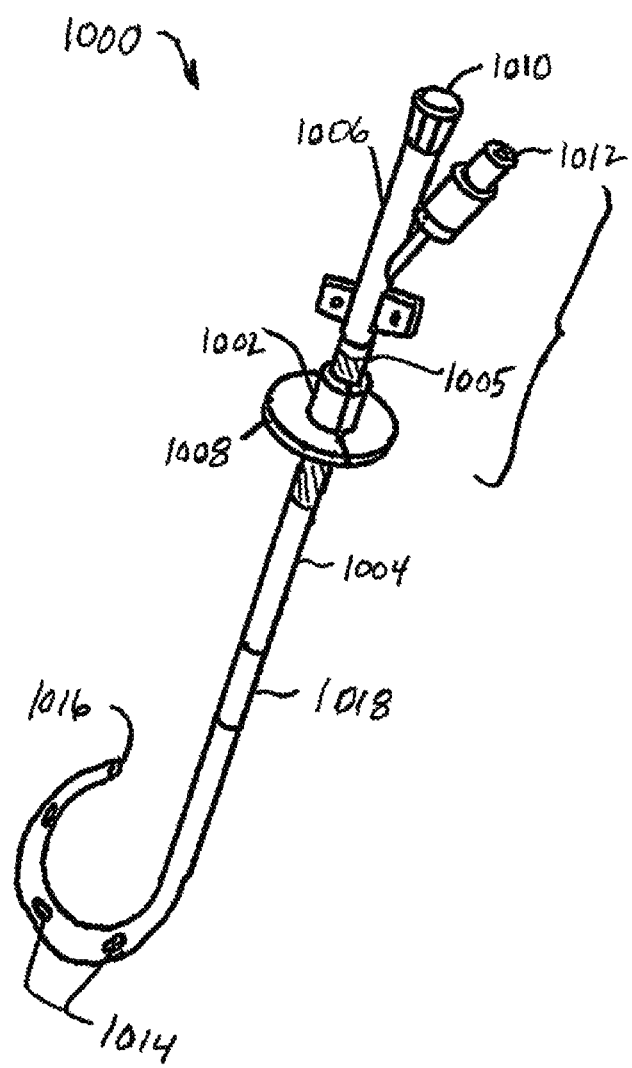
FIG. 10 illustrates a Velcro connection of a snugger device to an outer surface of a catheter, according to certain embodiments of the invention.

Referring to FIG. 10, a snugger device 1000 with a Velcro segment on an inner surface (not shown in detail in FIG. 10) of a column 1002 of the device 1000 is placed on a tube 1004 of a catheter 1006. The tube 1004 of the catheter 1006 includes a mating Velcro segment 1005 on an outer surface of the tube 1004. The snugger device 1000 includes a column 1002 connected to a flange 1008. The catheter 1006 includes a drain exit 1010 and an inflation port 1012. The drain exit 1010 is in fluid communication with ports 1014 located near a distal end 1016 of the catheter 1006. The inflation port 1012 is in fluid communication with a balloon 1018 surrounding the tube 1004 of the catheter 1006. The column 1002 of the snugger device 1000 substantially surrounds a circumference of the tube 1004 of the catheter 1006. The flange 1008 of the snugger device 1000 extends substantially perpendicular to the length of the tube 1004.

In operation, the catheter 1006 is inserted in conventional manner into an ostomy. The distal end 1016 of the catheter 1006 is lodged within a vessel, organ or other lumen. The balloon 1018 is inflated through the injection port 1012 to locate within the vessel, organ or other lumen. A fore portion 1020 of the catheter 1006 toward the drain exit 1110 and the injection port 1012 is located external to a body in which the catheter 1006 is positioned. The snugger device 1000 is placed on the tube 1004 of the catheter 1006 at the fore portion 1020. The fore portion 1020 is grasped and pulled to bring the inflated balloon 1018 into tensioned contact with the inner wall of the vessel, organ or other lumen at the ostomy. The snugger device 1000 is slid along the tube 1004 of the catheter 1006 to contact the skin or integument of a body in which the catheter 1006 is lodged, in order to snug the inflated balloon 1018 against the wall of the vessel, organ or other lumen. The snugger device 1000 is attached to the tube 1004 by the Velcro of the inner surface of the device 1000 and complementary Velcro 1005 on the outer surface of the tube 1004 to provide tension of the inflated balloon 1018 against the inner wall of the vessel, organ or other lumen.

In the foregoing, the particular tension provided by the snugger device for the balloon against the vessel inner wall will depend upon patient comfort and tolerance, effects on water tightness of the balloon against the inner wall, functional restoration of bladder cycling (separate filling/emptying), and patient satisfaction (snugged versus un-snugged). The balloon snugged to the inner wall of the vessel by the snugger device forms a more water tight connection of the catheter to the inner wall of the vessel.

A wide variety of alternatives are possible in the embodiments. The snugger device may be employed in many applications of catheters, intubations, and similar devices, and for other organ systems, conduits and reservoirs, such as for colostomies, nephrostomies, small bowel intestinal conduits and cardiac powerlines. The snugger device may be any desired shape, including, for example, the hollow column may be cylindrical, elliptical, square or rectangular or otherwise and the flange may be generally round, oval, spherical or otherwise. The snugger device may also be any size, for example, the hollow column may be about 0.25" to about 1" in length or otherwise, as desired, and the flange may be about 0.5" to about 3" in diameter or otherwise, as desired. Thickness of the snugger device may vary also as desired. Materials of the snugger device may include silicone, polyurethane, other polymer, plastic, rubber, composite, or otherwise, as well as any combination of materials.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention.

Benefits, other advantages, and solutions to problems have been described above with regard to specific embodiments. However, the benefits, advantages, solutions to problems and device(s), connection(s) and element(s) that may cause any benefit, advantage, or solution to occur or become more pronounced are not to be construed as a critical, required, or essential feature or element of any or all the claims. As used herein, the terms "comprises, "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A device for snugging a balloon of a catheter against an inner wall of a lumen serviced by the catheter, the catheter has an outer surface, the catheter extends from outside a body having an outer body surface and into the body through the lumen, comprising:
    a hollow column having a top end and a bottom end, forming a throughway sized to accommodate a tube of the catheter through the hollow column;
    a flange extending from the bottom end of the hollow column, the flange extends generally perpendicular to a length of the hollow column and in use situates against the outer body surface of the body; and
    a securement device of the hollow column fixed outside of a body serviced by the catheter, the securement device for attachment of the hollow column to an outside of the catheter protruding through the hollow column and tensioning between the balloon and the flange;
    wherein the securement device is a safety pin passed through the hollow column and the tube of the catheter to secure the device to the catheter.

2. A device for use with a catheter having an outer surface, comprising:
    a hollow cylindrical column having a top and a bottom, the hollow cylindrical column is pliable;
    a flange connected to the bottom, the flange is pliable;
    a connector to reversibly secure the hollow cylindrical column to the outer surface of the catheter; and
    a securement device of the hollow cylindrical column for securing the hollow cylindrical column to a tube of the catheter, the securement device for attachment of the hollow cylindrical column to an outside of the catheter protruding through the hollow column and tensioning between the balloon and the flange;

wherein the securement device is a safety pin inserted through the hollow cylindrical column and the tube of the catheter.

3. A method, comprising:

providing a snugger device to an external portion of a tube of a catheter having a balloon inflated within a lumen or space of a body;

tugging the catheter to bring the balloon into tensioned contact with an inner wall of the lumen or space; and positioning the snugger device in contact with skin of the body and outside of the body in order to maintain tensioned contact of the balloon with the inner wall; and securing the snugger device from positioning to the tube of the catheter to maintain tensioned contact of the balloon with the inner wall;

wherein securing is by a safety pin passed through the snugger device and the tube of the catheter.

\* \* \* \* \*